(12) United States Patent
Kaller et al.

(10) Patent No.: US 7,659,976 B2
(45) Date of Patent: Feb. 9, 2010

(54) DEVICES AND METHODS FOR INSPECTING OPTICAL ELEMENTS WITH A VIEW TO CONTAMINATION

(75) Inventors: Julian Kaller, Koenigsbronn (DE); Herbert Fink, Aalen (DE); Christoph Zaczek, Heubach (DE); Wolfgang Rupp, Schwaebisch Gmuend (DE)

(73) Assignee: Carl Zeiss SMT AG, Oberkochen (DE)

( * ) Notice: Subject to any disclaimer, the term of this patent is extended or adjusted under 35 U.S.C. 154(b) by 416 days.

(21) Appl. No.: 11/635,293

(22) Filed: Dec. 7, 2006

(65) Prior Publication Data

US 2007/0132989 A1   Jun. 14, 2007

Related U.S. Application Data

(60) Provisional application No. 60/749,374, filed on Dec. 12, 2005.

(51) Int. Cl.
*G01N 21/00* (2006.01)
(52) U.S. Cl. .................... 356/239.2; 356/239.1
(58) Field of Classification Search .............. 356/239.1, 356/239.2
See application file for complete search history.

(56) References Cited

U.S. PATENT DOCUMENTS

| | | | | |
|---|---|---|---|---|
| 5,390,160 A | * | 2/1995 | Sasaki | 369/53.12 |
| 5,814,156 A | * | 9/1998 | Elliott et al. | 134/1 |
| 5,963,315 A | * | 10/1999 | Hiatt et al. | 356/237.3 |
| 6,356,347 B1 | * | 3/2002 | Watanabe et al. | 356/369 |
| 6,392,738 B1 | * | 5/2002 | van de Pasch et al. | 355/30 |
| 2003/0011763 A1 | * | 1/2003 | Taniguchi et al. | 356/239.2 |

* cited by examiner

*Primary Examiner*—Gregory J Toatley, Jr.
*Assistant Examiner*—Juan D Valentin
(74) *Attorney, Agent, or Firm*—Walter A. Hackler

(57) ABSTRACT

Described is an examination system (1) for locating contamination (2) on an optical element (4) installed in an optical system (5), which examination system (1) comprises: a spatially resolving detector (6); imaging optics (7) that magnify in particular at a magnification of between 2 times and 100 times, for magnified imaging of a surface sub-region (3a) of the optical element (4) on the spatially resolving detector (6); as well as a movement mechanism (12), in particular a motorized movement mechanism (12), for displacing the imaging optics (7) together with the detector (6) relative to the surface (3) of the optical element (4) such that any desired surface sub-region of the surface (3) can be imaged at magnification.

29 Claims, 7 Drawing Sheets

DEVICES AND METHODS FOR INSPECTING OPTICAL ELEMENTS WITH A VIEW TO CONTAMINATION

BACKGROUND OF THE INVENTION

The present application claims priority from U.S. 60/749,374 filed Dec. 12, 2005. This referenced application is to be incorporated herein in its entirety.

The invention relates to the inspection of optical elements with a view to contamination, in particular to the determination of spatial distribution of contamination on the surface of optical elements, as well as to the determination of the composition of said contamination, with an examination system, an examination device and a manipulator. The investigated optical elements form part of an optical device, in particular of laser machining apparatus or projection illumination apparatus for microlithography. The invention also relates to an optical device that comprises such examination systems and examination devices or manipulators. Furthermore, the invention relates to a method for removing contamination from the surface of an optical element, as well as to a method for determining the thickness of contamination layers on optical elements.

Optical devices, in particular systems in which short-wave radiation is used, such as e.g. projection illumination apparatus for lithography optics, or systems for inspecting photomasks and wafers, as well as laser systems e.g. for laser machining apparatus, in particular UV laser systems and systems for guiding their beams, are associated with the danger that the surfaces of some of their optical elements become contaminated as a result of the atmosphere surrounding them.

Within the context of this patent application the term "atmosphere" refers to ambient air (including filtered or conditioned air), purge gases, immersion fluids and any impurities contained therein, as well as in the case of optical elements that are arranged in vacuum chambers the residual gases contained therein. The term "short-wave radiation" refers to UV light with wavelengths of less than 400 nm, in particular wavelengths of approximately 365 nm, 248 nm, 193 nm and 157 nm, as well as soft X-ray radiation, in particular in the region of 13.5 nm. The term "optical element" refers to a lens, mirror, base plate, grid or any other optical element.

Within the context of this patent application, the term "laser machining apparatus" relates to a material processing apparatus, in particular to a laser annealing apparatus which is useful in annealing of large substrates, in the field of flat panel display, such as liquid crystal display, or luminescence display manufacturing processes as well as in the fabrication of thin film photovoltaic devices. Such an apparatus allows for crystallization procedures such as excimer laser crystallization (ELC), sequential lateral solidification (SLS) or thin beam crystallization procedure (TDX). In particular, such an apparatus is useful in order to crystallize amorphous Silicon (a-Si) films forming polycrystalline Silicon (p-Si). Such polycrystalline Silicon thin films are widely used in microelectronics and display techniques as mentioned above. P-Si has a higher charge carrier mobility as compared to a-Si which is useful for the fabrication of higher speed switching or integration of higher quality driver electronics on the display substrate. Furthermore, p-Si has a lower absorption coefficient for light in the visual spectral range enabling p-Si to be used as a rear electrode for LCD-applications allowing backlight to be transmitted. Lastly, the defect density of p-Si is lower as compared with a-Si which is a prerequisite for the fabrication of high efficient solar cells. The conversion of a-Si into p-Si may be employed by heat treatment at around 1000° C. Such a procedure may only be used for a-Si on heat resistant substrates such as quartz. Such materials are expensive compared to normal float glass for display purposes. Light induced crystallization of a-Si allows the formation of p-Si from a-Si without destroying the substrate by the thermal load during crystallization. Amorphous Silicon may be deposited by a low cost process such as sputtering or chemical vapour deposition (CVD) on substrates such as glass, quartz or synthetics.

It is well known that contamination of optics by trace gases in the ambient atmosphere can have various causes so that contamination in its spatial arrangement and in its composition can differ considerably. Despite different characteristics in relation to the topography and/or chemical composition, contamination has at least in part the same effect on those optical characteristics of the optical system, which characteristics are demanded by the user to serve the intended purpose.

A typical example of the above relates to scattered light in an imaging optics system. Light that does not contribute to imaging but instead impinges upon the image plane at some other point is generally referred to as scattered light. For example in the case of projection illumination apparatus for the semiconductor industry, scattered light is an important criterion for the usability of the optical system. Usually, scattered light is regularly measured and monitored by the projection illumination apparatus at the system plane (i.e. at the location of the wafer), wherein an increase in scattered light indicates the presence of contamination.

However, the known methods for measuring scattered light in an optical system cannot unequivocally locate the source of the scattered light, wherein e.g. the depositing of material on at least one optical surface of the optical system is considered to be one possible source. Depending on the type of contamination (which in turn depends on the ambient atmosphere) the topography and chemical composition of this material can however be quite different, as described above.

Known materials that deposit on the optical surfaces include in particular: salts, in particular sulphates and phosphates, as well as chlorides, nitrites and nitrates with ammonium- or alkali- or alkaline earth metals as counter-ions. Furthermore, the depositing of thin films comprising hydrocarbons, as well as films comprising polymer materials rich in hydrocarbons, are known, as is the depositing of layers of polymeric Si compounds that arise as a result of the effect of light on siloxanes.

Apart from deposits, scattered light can also result from changes in the surface of the optical elements, e.g. by the etching of optical elements and/or of layers thereon, or by the chipping off of layers on optical elements. Furthermore, scattering centres can form in the material of the optical elements, e.g. as a result of blistering, changes in the homogeneity, formation of microchannels or microcracks.

US 2005/0094115 A1 describes projection illumination apparatus with an examination device for examining an optical element for contamination. The examination device comprises a light generation unit that radiates light onto the optical element, a photodetector that detects light transmitted or reflected by the optical element, as well as a processing device, connected to the photodetector, for processing the data measured by the detector. Preferably, by means of the examination system the reflectivity or the transmissivity of the optical elements is measured and compared to desired values. Projection illumination apparatus described therein further comprises devices for removing contamination from optical elements.

From DE 103 32 110 A1 of the applicant, furthermore a device for scattered-light inspection of optical elements is known, which device at least in part can be accommodated in a reticle holder or substrate holder of projection illumination apparatus for microlithography, and to this effect is accommodated in a suitable housing.

From DE 102 10 209 A1 by the applicant, a method and a device for scattered light inspection of transparent optical elements, in particular of blanks for optics components are known, in which method and device an examination light beam is guided through the optical element, and the scattered light is recorded that originates from a volume region of the optical element, through which volume region the examination light beam travels. In this arrangement, by means of a movable mirror, the examination light beam can be guided in a scanning manner along the entire extent of the optical element, and/or the specimen to be examined is mounted on an x-y translational table and is moved in a suitable manner so that a two-dimensional scattered-light map of the specimen to be examined can be produced.

SUMMARY OF THE INVENTION

According to a first aspect of the invention, an examination system is to be provided by means of which contamination on an optical element installed in an optical system can be located.

According to a further aspect of the invention, an optical device, preferably laser machining apparatus or projection illumination apparatus for microlithography is to be provided, in which optical device contamination on at least one of its optical elements can be located.

According to a further aspect of the invention, an examination device for inspecting an optical element, which has been integrated in an optical system, for contamination is to be provided, as is an optical device, such as laser machining apparatus or projection illumination apparatus for microlithography, which optical device comprises such an examination device.

According to a further aspect of the invention, a manipulator and an optical device, in particular laser machining apparatus or projection illumination apparatus for microlithography with such a manipulator are to be provided, by means of which the composition of contamination on an optical element can be determined.

A further aspect of the invention relates to the provision of a method for locating contamination on the surface of an optical element integrated in an optical system.

According to a further aspect of the invention, a method for removing contamination on surfaces of optical elements installed in optical systems is to be provided.

According to a further aspect of the invention, a method for determining the thickness of a contamination layer on the surface of an optical element installed in an optical system is to be stated.

According to the first aspect of the invention, this object is met by an examination system for locating contamination on an optical element installed in an optical system, comprising: a spatially resolving detector; magnifying imaging optics that magnify in particular at a magnification of between 2 times and 100 times, for magnified imaging of a surface sub-region of the optical element on the spatially resolving detector; as well as a movement mechanism, in particular a motorised movement mechanism, for displacing the imaging optics together with the detector relative to the surface of the optical element such that any desired surface sub-region of the surface can be imaged at magnification.

By means of the examination system according to the invention, optical elements in the installed state in optical systems can be examined for contamination, without the need for said optical elements to be removed from said optical systems. Magnified imaging makes it possible to precisely locate contamination on the surface. By means of the movement mechanism, in the case of imaging at magnification of a sub-region of the surface, the examination system can be moved in a scanning manner along the surface so that a map of the entire surface can be achieved at significantly greater resolution than would be possible if the entire surface were to be covered and imaged using the magnifying imaging optics. When the surface quality of the optical element is known, conclusions relating to its scatter behaviour can be drawn and in particular those instances of contamination can be precisely located, which instances cause a particularly strong scattered-light fraction. If applicable, such contamination can then be removed in a targeted manner from the surface, or conclusions can be drawn as to when it will become necessary to exchange the optical element, or as to which cleaning method is particularly suitable for removing the contamination. Typically the percentage of the individual surface sub-regions of the entire surface of the optical element is less than 10%, preferably less than 5%, in particular less than 1%. Preferably, the movement mechanism operates in a motorised manner; however, as an alternative manual displacement is also possible. In the context of this application, in the case of transmissive optical elements such as lenses or base plates, the term "below the surface of an optical element" refers to the front or rear of the optical element.

In an advantageous embodiment the movement mechanism comprises two translatory drives for displacing, relative to the optical element, the imaging optics together with the detector along at least two displacement axes that are located in a common plane, wherein the displacement path along each of the axes is preferably more than 10 cm, particularly preferably more than 20 cm, in particular more than 30 cm. The two displacement axes are preferably arranged so as to be perpendicular in relation to each other, with the movement mechanism being formed by an x-y translational table. In this arrangement the displacement path matches the diameter of the optical element to be examined so that the imaging optics can cover each surface sub-region of the optical element in that said imaging optics travel essentially parallel in relation to the surface.

In a preferred improvement the movement mechanism comprises a third translatory drive for displacing the imaging optics together with the detector along a third axis that is not positioned in the shared plane, wherein the displacement path along the third axis preferably measures more than 5 mm, in particular more than 2 cm. The third displacement axis is used for adjusting the distance between the imaging optics and the surface to be examined so that it can be ensured that the object plane of the magnifying imaging optics always comes to rest on the surface to be examined. This is advantageous because the examination system can be used in optical systems of various types, in which systems the possible design arrangement of the examination system and in particular the spacing between the examination system and the surface to be examined can vary. Furthermore, because of the possibility of displacement perpendicularly in relation to the surface, even in the case of curved surfaces, the object plane can be essentially spaced apart by the same distance from the surface, which facilitates the preparation of a two-dimensional map of the surface. Furthermore, by a displacement movement perpendicular to the surface, it is also possible to prepare a three-dimensional map of curved surfaces. The three translatory drives are preferably designed as NC axes; they can in particular be driven wirelessly by way of a PC or a laptop. For the purpose of carrying out serial testing, specified travel movements of the displacement axes can be stored either in a memory of the examination system or externally; consequently inspection of the surface is greatly simplified and can be carried out in an automated manner. This makes possible recurrent quick readings without the optical system becoming inoperative for long when the readings are taken. In this way a trend in the build-up of contamination can be determined, which makes it possible to estimate the remaining service life of the optical element before cleaning or an exchange of the element becomes necessary.

In a preferred exemplary embodiment the movement mechanism comprises a tilting mechanism, preferably a swivellable arm, for unrestricted spatial orientation of the examination system relative to the surface. By tilting the examination system it can be ensured that even in the case of a curved surface the normal vector of the surface sub-region that is imaged at the time is always positioned so as to be perpendicular to the object plane, i.e. in a line with the optical axis of the imaging optics. In this way it can be ensured that the entire surface sub-region is imaged on the image field so as to be in focus. In contrast to this, when the optical axis of the imaging optics is arranged at an angle in relation to the surface normal, usually only a section of the image field can be imaged so as to be in focus. Such tilting can also be advantageous in the case of optical elements with planar surfaces, in particular if the examination system can only be positioned in the optical system in such a manner that the displacement axes of the examination system are arranged at an angle to the normal vector of the surface. This can for example be the case in the inspection of mirror surfaces that are arranged in an enclosed optical system.

In a further preferred embodiment the examination system comprises a light generating unit with a light emission area, which light generating unit is preferably arranged laterally between the imaging optics and the optical element, for radiation of illumination light onto the optical element. Usually light at wavelengths in the visible spectrum is used as illumination light. In particular in the case of optical elements that are designed for wavelengths in the UV range, as an alternative it is also possible to use illumination light with a wavelength that is spectrally close to the useful wavelength or corresponds to said useful wavelength, because the characteristics of the surface become clearer the closer the wavelength of the illumination radiation approaches the useful wavelength. To this effect the imaging optics and the detector might have to be designed such that they can image or register radiation of the useful wavelength. A light emission area of the light generating unit is preferably arranged laterally between the optical element and the imaging optics so as to, in the case of transmissive optical elements, prevent the illumination radiation entering the optical system through said optical element and thus causing scattered light in said optical system, which scattered light can have a negative effect on imaging. This can in particular be avoided if the light generating unit is arranged such that the illumination light hits the surface at glancing incidence.

In a further particularly advantageous embodiment the focal length of the imaging optics, which focal length is on the side of the object, measures more than 3 cm, preferably more than 5 cm. In this way a situation can be avoided where for the purpose of positioning the object plane on the optical element the imaging optics have to be moved so closely to the optical element that if the examination system is incorrectly positioned, the latter establishes contact with the surface, which can lead to the formation of scratch marks on the surface of the optical element.

In a particularly advantageous embodiment, the imaging optics comprise zoom optics for variable, in particular infinitely variable, setting of the magnification. In this way it is possible, for example, to first view the surface of the optical element at low magnification, wherein individual sub-regions of the surface that are particularly heavily contaminated can be examined separately by displacing the examination system and subsequent viewing at higher magnification.

In a further advantageous embodiment, the detector is a CCD array. This array makes possible fast readout of the measuring data so that the surface to be examined can be scanned at high speed. Of course other spatially resolving detector types are also possible, in particular CMOS image sensors, diode arrays or discrete photodiode units or photomultiplier units.

In a further preferred embodiment the examination system comprises a data processing unit that is connected to the detector, for evaluating measuring data of the detector. In particular during scanning of the surface, the data processing unit puts the measured sub-images together so that they form a uniform two-dimensional or three-dimensional map of the surface. This map can either be used for assessment by an operator, or an automatic comparison of the measuring data with known data relating to contamination can be carried out in the data processing unit so that conclusions can be drawn as to the type of contamination. Furthermore, the data processing unit advantageously comprises a device for storing and displaying the stored data, as well as a transmission unit, in particular for wireless transmission of the measuring data, e.g. to a PC.

In a preferred embodiment the examination system comprises a unit for removing contamination. This unit can, in particular, be an ultrasonic cleaning unit, a contact cleaning unit, a unit for applying a cleaning solution, a radiation unit, a plasma cleaning unit, or a unit for applying a cleaning gas (active gas).

In a further particularly preferred embodiment, the examination system is dimensioned such that it can be accommodated in a holder of an optical device, preferably a mask holder or a substrate holder of projection illumination apparatus. In this arrangement the examination system is in particular mobile, i.e. the weight and design of the examination system make it possible to easily move said examination system from an optical system to be examined to another optical system. In order to use the examination system in projection illumination apparatus for microlithography, it is particularly advantageous if the examination system is integrated in a housing that can be placed into the apparatus instead of the mask or the substrate. In this way it is possible, for example, to examine in a particularly simple manner the closing element of a projection lens or of an illumination system in the apparatus.

According to a second aspect of the invention, the object is met by an optical device, in particular a laser machining apparatus or projection illumination apparatus for microlithography for imaging a structure on a photomask onto a light-sensitive substrate, the optical device comprising: at least one optical element and an examination system for locating contamination on the optical element, wherein the examination system comprises: a spatially resolving detector, and imaging optics that magnify in particular at a magnification of between 2 times and 100 times, for magnified imaging of the entire surface or of a surface sub-region of the optical element on the spatially resolving detector.

The optical device, e.g. projection illumination apparatus comprises an examination system that is stationary, i.e. it is permanently in place in said projection illumination apparatus, which examination system makes possible magnified imaging of the surface of an optical element onto the detector. The examination system can be installed in particular in the reticle stage or in the wafer stage of the projection illumination apparatus. However, the examination system can also be arranged on a separate stage that can be exchanged with a wafer stage on which the substrate is arranged, as is explained in more detail in US 2005/0094115 A1. In contrast to the examination system shown in this printed publication, with the projection illumination apparatus according to the invention magnified imaging of the surfaces of optical elements can be carried out so that improved location of contamination on the surface can take place.

In a particularly preferred embodiment the examination system of the optical device comprises a movement mechanism, in particular a motorised movement mechanism, for displacing the imaging optics together with the detector relative to the surface of the optical element such that any desired surface sub-region of the surface can be imaged so as to be magnified. In this case the examination system is essentially identical to the above-described examination system, except that in the present case the examination system is installed in the projection illumination apparatus or the laser machining apparatus so as to be stationary. As far as preferred embodiments of the examination system in the optical device according to the invention are concerned, reference is made to the explanations provided above in the context of the examination system described above. The optical device can in particular also comprise a unit for removing contamination, as explained above.

In a particularly advantageous embodiment of the optical device, the surface of the optical element, which surface is to be examined, is a closing element of a closed optical system, in particular of an illumination system or of a projection lens of a projection illumination apparatus. In this arrangement the examination system is advantageously designed such that it can be arranged in a mask holder or a substrate holder of the projection illumination apparatus.

In a particularly advantageous embodiment, the optical element to be examined is a closing element of the projection lens, which closing element is arranged so as to face the light-sensitive substrate. Such closing elements are particularly susceptible to contamination because, during illumination mode, contaminating gases can emanate from the substrate and can contaminate the surface that faces the substrate.

In a further particularly preferred exemplary embodiment the optical element is in particular a reflective optical element that is arranged in the interior of a vacuum chamber, wherein the examination system is arranged outside the vacuum chamber. Typically a window has been provided in the vacuum chamber, by means of which window the inspection can be carried out. In this arrangement, by way of the movement mechanism and if applicable the tilting mechanism, the examination system can be aligned to individual optical elements in the vacuum chamber, and through the window the surfaces of these elements can be imaged even over substantial distances. In this way the in-situ inspection of optical elements in vacuum chambers is made possible without the vacuum having to be released for the inspection. This is in particular advantageous in the case of EUV projection illumination apparatus, whose reflective optical elements are operated in a vacuum. In this arrangement, in particular, an examination system can be used that can be freely oriented in space and that comprises zoom optics so that the optical elements in the vacuum chamber can be driven in a targeted manner for inspection.

In a further preferred embodiment the examination system and the optical element are arranged in the interior of a vacuum chamber, wherein the movement mechanism preferably comprises a swivellable arm. By means of the swivellable arm the examination system can be used for examining several optical elements arranged in the vacuum chamber. In this arrangement the examination system can be driven from outside the chamber so that the vacuum does not have to be released for the purpose of inspection.

According to a further aspect of the invention, the object is met by an examination device for inspecting an optical element for contamination, with the examination device comprising: a light generating unit with a light emission area for directed radiation of light onto the optical element, a detector for registering the light reflected by the optical element, as well as a movement mechanism, in particular a motorised movement mechanism, for displacing the light emission area of the light generating unit, preferably together with the detector, along the surface of the optical element such that a predefinable, in particular constant, distance between the light emission area and the surface can be maintained.

The examination device according to the invention can be moved, by the movement mechanism, along the surface of the optical element so that it is possible to vary the location at which the light radiated in is reflected by the surface of the optical element. This makes it possible to undertake scanning measuring of the surface characteristics of the optical element, without the element itself having to be moved. The examination device is therefore in particular suitable for inspecting optical elements in their installed state in optical systems. The examination device can be used for measuring scattered light, as described in DE 103 32 110 A1 in the context of a device that does not comprise a movement mechanism. As an alternative, or in addition, it is also possible to use the detector for measuring a light fraction that is reflected in a specular manner, i.e. non-scattered (angle of incidence=angle of reflection), by the surface of the optical element. Advantageously the detector is designed for measuring the intensity of the reflected radiation and can, in particular in the case of scattered-light measuring, be used as a spatially resolved flat detector for concurrently measuring several scatter angles. As an alternative, the detector can also be designed as a wavelength-sensitive detector, by means of which the spectral (wavelength-dependent) reflectivity of the surface can be determined. The distance between the light emission area and the surface during displacement along the surface is preferably kept essentially constant in both cases. The movement mechanism can, in particular, comprise a memory unit in which the travel path necessary for specified surface shapes is stored. In this case, after initial positioning of the examination device in a defined position in relation to the surface, measuring of the surface can then take place in a fully automated manner.

In a preferred embodiment, the movement mechanism comprises two translatory drives for displacing the imaging optics together with the detector along two axes situated in a shared plane, wherein the displacement path along each of the axes preferably measures more than 10 cm, particularly preferably more than 20 cm, in particular more than 30 cm. As a result of the two displacement axes, which are in particular orthogonal in relation to each other, the examination device can be displaced so as to be essentially parallel in relation to a planar surface of the optical element so that in this case a predefinable distance from the surface can be maintained.

In a preferred improvement of this embodiment, the movement mechanism comprises a third translatory drive for displacing the imaging optics together with the detector along a third axis, which is not situated in the shared plane, wherein the displacement path along the third axis preferably measures more than 5 mm, in particular more than 2 cm. The third displacement axis is used to adjust the distance between the imaging optics and the surface to be examined. In this way the distance between a light emission area of the light generating unit and the surface can be held so as to be essentially constant even when scanning curved surfaces.

In a preferred embodiment, the movement mechanism comprises a tilting mechanism, preferably a swivellable arm, for unrestricted spatial orientation of a light emission area of the light generating unit of the examination device relative to the surface. By tilting the light generating unit it can be ensured—in particular when perpendicular light incidence onto the surface is desired—that even in the case of a curved surface the normal vector of the surface sub-region that is being imaged at the time can always be aligned so as to be perpendicular to the light emission area.

In a further particularly preferred embodiment, the light generating unit for generating light comprises at least two wavelengths, with the detector being wavelength-sensitive. The examination light can be radiated, at various wavelengths either offset in time or concurrently, onto the surface of the optical element. Apart from measuring scattered light with at least two wavelengths, as described in more detail in DE 103 32 110 A1 which is incorporated by reference to the content of this application, the use of several wavelengths when measuring the specularly reflected light can also be used to determine the thickness of essentially homogeneous surface layers on optical elements with a reflection-reducing or reflection-increasing layer system, as described in more detail below.

In a particularly advantageous embodiment, the detector is designed to register the light that is specularly reflected by the optical element. To this effect, said detector is arranged, in relation to the surface of the optical element and the light emission area of the light generating unit, such that essentially specularly scattered light impinges upon the detector surface.

In an extremely preferred embodiment, the light generating unit comprises a fibre-optical light guide for feeding the light to the optical element and preferably for returning the light reflected by the surface. In the case of returning the light through the fibre-optical light guide it is not absolutely essential for the light emission area of the fibre-optical light guide to be arranged so as to be perpendicular in relation to the surface normal of the surface, because the light supplied by the fibre-optical light guide is a spherical wave. When the emission area of the fibre-optical light guide is positioned in direct proximity to the surface, a sufficiently large fraction of the reflected light enters the fibre-optical light guide, which light can, for example, be decoupled at the end of the fibre-optical light guide, which end is opposite to the light emission area, and which light is fed to the detector. For such measuring with the use of a fibre-optical light guide it is necessary for its light emission area to be arranged in direct proximity of the surface of the optical element, i.e. at a distance of typically less than 1 mm so that measuring in the near field can be carried out. In this case all the wavelengths used for measuring can be fed in and carried away concurrently through the fibre-optical light guide, a situation which is associated with a substantial gain in time during scanning of the surface. As an alternative, the fibre-optical light guide can only be used for feeding the light to the surface.

In a preferred embodiment, the light emission area of the light generating unit is formed by a recess in a spatially resolving detector surface, in particular at the centre of a circular detector surface, wherein light emission preferably takes place parallel in relation to the detector surface. With the spatially resolving detector surface, spatially resolved scattered-light measuring is carried out, in which the angular region that is covered at a given distance to the surface is delimited upwards by the detector diameter, and downwards by the diameter of the recess. With perpendicular radiation of the light onto the surface the specularly reflected light is fully reflected into the recess if the distance has been suitably selected so that the surrounding detector surface is not impinged upon by this light and in this way saturation of the detectors can be prevented. The detector surface can comprise several modules, wherein preferably CCD arrays are used as detector surfaces. Preferably, the light generating unit comprises a beam forming unit for focusing the light beam onto the surface.

In a further preferred embodiment, the examination device comprises a distance measuring device for determining the distance of a light emission area of the light generating unit relative to the surface. In this way it can be ensured that the examination device does not touch the surface, a situation which is advantageous in particular if the light emission area of said examination device is arranged only a short distance from the surface.

In a further particularly preferred embodiment, the examination device comprises a control device for controlling the distance of the light emission area of the light generating unit relative to the surface of the optical element. In this way, during scanning, an essentially constant distance between the light emission area and the surface of the optical element can be maintained. As an alternative, as described above, this can also take place by specifying a travel path that has been predefined for a particular surface shape.

In a further particularly preferred embodiment, the light generating unit is designed for generating light with wavelengths in the ultraviolet spectral range between 180 nm and 400 nm, in the visible spectral range, or in the infrared spectral range. In principle it is preferable for the light generating unit to generate light with a wavelength close to the useful wavelength of the optical system because in this case the optical characteristics of the surface at the wavelength used in operation can be determined. With the use of wavelengths in the IR range, a chemical fingerprint of the surface can be produced.

In a preferred embodiment the examination device comprises a data processing unit, connected to the detector, for evaluating the measuring data of the detector. This unit preferably comprises devices for storing and visualising the measuring data, and/or a transmission unit, preferably for wireless transmission of the measuring data to a spatially separate unit, in particular to a PC.

In a further particularly preferred embodiment, the examination device comprises a unit for removing contamination. This unit can, in particular, be an ultrasonic cleaning unit, a contact cleaning unit, a unit for applying a cleaning solution, a radiation unit, a plasma cleaning unit, or a unit for applying a cleaning gas (active gas).

In a further particularly preferred embodiment, the examination device is dimensioned such that it can be accommodated in a holder of an optical device, in particular a mask holder or a substrate holder of projection illumination apparatus. To this effect the examination device is designed to be as flat as possible and comprises a correspondingly adapted housing.

According to a further aspect of the invention, the object is met by an optical device, in particular a laser machining apparatus or projection illumination apparatus for microlithography for imaging a structure on a photomask onto a light-sensitive substrate, the optical device comprising at least one optical element and an examination device as described above. The examination device is arranged so as to be stationary in the optical device, and can, in particular, be used for inspecting closing elements of an illumination system or of a projection lens in the apparatus, if said device is integrated in the reticle stage or wafer stage.

In a preferred embodiment the optical device comprises an examination system according to the first aspect of the invention. In this case the examination system for magnified imaging of the surface, and the examination device for measuring the scattered or specularly reflected light can be used in combination so that the nature of contamination can be determined by means of two different methods. It goes without saying that the examination system and the examination device preferably only comprise one shared movement mechanism.

According to a further aspect of the invention, the object is met by a manipulator for sampling the surface of an optical element, comprising: a detachment unit for detaching contamination from the surface of the optical element, and a movement mechanism, in particular a motorised movement mechanism, for displacing the detachment unit relative to the surface of the optical element such that contamination can be detached at any desired position on the surface.

By way of the manipulator a sample of the contamination can be removed from the optical element and can subsequently be chemically analysed. The chemical analyser can either be part of the manipulator, or the sample can be removed from the manipulator and can be examined in a spatially separate chemical analysis unit. By way of chemical analysis the chemical composition of the contamination can be determined. If the type of impurity is known, e.g. if it is sulphur, it is possible to look in a targeted way for any materials that might outgas sulphur. If the source of impurities is known, suitable countermeasures can be initiated. Furthermore, the most advantageous way of removing the contamination can be determined.

The detachment unit is guided by the movement mechanism, which can e.g. comprise a movable arm, preferably a swivellable arm, in particular a telescopic arm, wherein the movement mechanism is preferably designed for translatory movement on three axes and if need be comprises a tilting mechanism for rotation on two further axes, as explained in more detail above in the context of the examination system and the examination device.

In a particularly preferred embodiment, the manipulator comprises a container for accommodating the contamination removed from the surface, which container preferably contains a solvent. The container can be designed to accommodate the sample in solid, liquid or gaseous form, depending on the type of the detachment unit, wherein the contamination can preferably be dissolved in the solvent.

In an advantageous embodiment the detachment unit comprises a wire loop or a woven fabric, which preferably has been impregnated with solvent, for removing the sample by mechanical contact with the surface. The manipulator can also comprise a miniaturised scraper or a blade by means of which a sample of the contaminating substances can be removed without damaging the surface of the optical element.

In a further preferred embodiment, the detachment unit comprises a light generating unit, in particular an IR laser, for directed radiation of light onto the surface. Using laser light at high strengths of radiation, part of the contamination can be detached (sputtered) or evaporated.

In a further particularly preferred embodiment, the detachment unit comprises a capillary, preferably for applying a solvent to the surface. The liquid solvent in the form of droplets is made to contact that part of the surface that is contaminated. Part of the contamination is dissolved in the solvent and is collected in liquid form. Preferably water or an organic solvent, e.g. methanol, is used as a solvent, depending on the nature of the surface (hydrophilic or hydrophobic) and if applicable on the nature of the contamination. As an alternative, the capillary can also be used for sucking the contamination from the surface.

In a further particularly preferred embodiment, the manipulator comprises a suction unit for sucking the contamination from the surface. By means of the suction unit, the sample can easily be placed into a container provided for storage.

The invention is also implemented in an optical device, in particular a laser machining apparatus or projection illumination apparatus for microlithography for imaging a structure onto a light-sensitive substrate, the optical device comprising at least one optical element and a manipulator, as described above. In this arrangement the manipulator is used for removing samples from the surface.

In a particularly advantageous embodiment the optical device comprises an examination system or an examination device as described above. With the use of the examination system or the examination device a suitable position for sampling can be selected. In particular when two different contaminating materials are arranged directly side-by-side, by determining the topography a suitable place for sampling can be determined, and furthermore an estimate can be made of the quantity of the sample that is required for chemical analysis. By way of chemical analysis, information concerning the nature of the contamination can be fed to the examination device, which information can in particular in the case of thin contamination films be used to calculate the thickness of the contamination layer (see below).

In a further particularly preferred embodiment, the optical device comprises a unit for removing contamination. This unit can, in particular, be an ultrasonic cleaning unit, a contact cleaning unit, a unit for applying a cleaning solution, a radiation unit, a plasma cleaning unit, or a unit for applying a cleaning gas (active gas). Several options for designing such a unit are described in US 2005/0094115 A1, which by way of reference becomes part of the content of the present application.

According to a further aspect of the invention, the object is met by a method for locating contamination on the surface of an optical element, in particular by means of an examination system according to the first aspect of the invention, comprising the steps of: (a) magnifying imaging of the entire surface or a surface sub-region of the optical element; and (b) detecting the magnified image of the entire surface or surface sub-region. Preferably, the steps (a) and (b) are carried out in relation to a plurality of surface sub-regions, in particular of adjacent surface sub-regions, the method further comprising the step of: (c) producing a map from the plurality of magnified images. By means of magnifying imaging of surface sub-optical which can in particular be composed by a data processing device to form a map, a high-resolution image of the surface of the optical element to be examined can be taken, which image far exceeds the image field of the examination system. In this way even curved surfaces of optical systems can be acquired in a two-dimensional manner. When the entire surface is to be imaged all at once, usually the focal depth of the imaging optics used is not sufficient to generate an in-focus image of the surface.

In a preferred variant of this method, in respect of each surface sub-region, the object plane of the magnifying imaging optics is varied perpendicularly to the surface, and in step (c) a three-dimensional map of the surface is produced from the plurality of magnified images. By means of the variation in the object plane, three-dimensional measuring data of the surface can be collected, which in step (c) by way of superposition in a suitable data processing unit can be joined to form a three-dimensional map of the surface. Of course this method can also be carried out in relation to only a single surface sub-region, which e.g. is particularly badly contaminated. This method is particularly advantageous if the depth of focus of the optics used is less than that of the surface roughness so that even on a surface sub-region the entire surface cannot be imaged so as to be in focus.

In a preferred variant the enlarged image detected in step (b), or the map produced in step (c), is evaluated to locate the contamination. It is thus optionally possible to individually examine for contamination each of the images generated in step (b), or to wait until the entire surface has been scanned, before using the map produced in this manner for the purpose of locating contamination.

A further aspect of the invention relates to a method for removing contamination from the surface of an optical element installed in an optical system, comprising the steps of: (a) acquiring measuring data that is significant in relation to the nature of contamination on the surface; (b) evaluating the measuring data and comparing the evaluated data with known data that is significant in relation to the nature of contamination; (c) selecting a cleaning method, from a group of cleaning methods, for removing the contamination depending on the result of the comparison carried out in step (b); and (d) removing the contamination by applying the selected cleaning method. By determining measuring data that is relevant in relation to the nature of contamination, and by subsequent comparison with known measuring data, the nature, in particular the spatial arrangement, the type or thickness of contamination can be acquired, and a suitable cleaning method can be selected. In the context of this application, the term "suitable cleaning method" also includes at least temporary omission of cleaning in step (d). Furthermore, the term "suitable cleaning method" also includes the option of removing the optical element from the optical system if it is recognised that complete removal of the contamination is not possible using the cleaning procedures available in the optical system, or if such cleaning is associated with the danger of completely destroying the surface, which can be the case in particular with already partially delaminated surfaces.

In a particularly preferred variant the cleaning process is selected from the group comprising ultrasonic cleaning, contact cleaning, applying a cleaning solution, exposure to radiation, application of a cleaning gas, and plasma cleaning. In the method according to the invention, these and further suitable cleaning methods can also be applied in combination if it is known, for example, that pre-cleaning by means of a first method improves cleaning by means of a second method.

In a further particularly preferred variant in a preceding method step allocation of cleaning methods and known data that is significant in relation to the nature of the contamination takes place. The allocation can take place in a table in which suitable cleaning methods are stored in relation to known types, positions and thicknesses of contamination. During comparison of the evaluated data with known data, the evaluated data is associated with that known data with which it shows the best agreement. If during this comparison it is determined that the contamination involves salts, an aqueous cleaning solution is particularly advantageous. In the case of contamination by siloxanes, plasma cleaning is a likely method as it is in the case of hydrocarbons, which can, for example also be removed with the use of ozone.

In a further particularly preferred variant, following step (d), for the purpose of assessing the success of the cleaning method used, at least step (a) is repeated. Should this assessment determine that cleaning was insufficient, in subsequent method-related steps, depending on the degree of success, either renewed cleaning using the same cleaning method, or cleaning using some other cleaning method can be carried out.

In a further advantageous variant, evaluation of the measuring data in step (b) comprises the preparation of a two-dimensional or three-dimensional map of the surface. By means of the map, the positions can be determined in which contamination is located on the surface of the optical element so that such contamination can be removed in a targeted manner.

In an advantageous variant, in step (a) measuring data that is significant in relation to the nature of contamination is determined by microscopy. Various types of contamination frequently have a characteristic microscopic "signature", i.e. a structure which becomes visible only with magnified imaging. With the use of such typical microscopic structures it is possible, for example, to differentiate between salt crystals and delamination or scratching on the surface. In a particularly preferred improvement of this variant, in step (b) during evaluation of the measuring data, in particular by determining the quantity per unit area and the size of the scattering structures, the scatter behaviour of the surface is calculated. In this arrangement the scatter behaviour can, for example, be calculated from the topography of the surface, which topography has been determined using microscopy. The calculated scatter behaviour can be compared with a desired scatter behaviour, depending on which comparison a determination can be made as to whether cleaning with the use of a suitable cleaning method is to be carried out. The scattered light of contaminated surfaces can be greater by an order of magnitude than the scattered light of non-contaminated surfaces.

In an advantageous embodiment, from the scatter behaviour of the surface, the component of contamination in the scattered light of the optical system is determined. The scatter behaviour of the surface is defined as the intensity of the scattered light depending on the scatter angle. If the scatter behaviour is known, the component of the scattered light caused by contamination on the optical element in relation to the entire scattered light of the optical system can be determined. To this effect the entire scattered light of the optical system can be measured at a suitable location, e.g. in the image plane, or the scattered light of the optical system is calculated by simulation. If the scattered light component generated by the optical element is above a predefined value, e.g. >1% of the entire scattered light generated by the system, then cleaning with a suitable cleaning method can be carried out.

In a further preferred variant, in step (a) the measuring data of the surface, which data is significant in relation to the nature of the contamination, is determined by scattered-light measuring. Such scattered-light measuring can be carried out by scanning a plurality of points on the surface of the optical element; in this way it is also possible to draw conclusions relating to contamination.

In a further preferred variant, in step (a) the measuring data of the surface, which data is significant in relation to the nature of the contamination, is determined by taking a sample from the surface and by chemical analysis of the sample.

In a particularly preferred variant, in a preceding step a suitable position for taking the sample from the surface is determined, e.g. by means of microscopy or spectroscopy.

In a particularly advantageous variant, a reflection-reducing or reflection-increasing layer system is applied to the surface, and in step (a), for the thickness of a contamination layer on the surface, significant measuring data is determined by measuring the reflectivity of the optical element at a plurality of wavelengths. It is well known to apply reflection-reducing or reflection-increasing layer systems to transmissive or reflective optical elements, which layer systems typically comprise dielectric individual layers, of alternating high and low refractive indices. A contamination layer on these layer systems can significantly reduce their effect. From the thickness of the layer it is for example possible to draw conclusions relating to the duration required for carrying out a cleaning method for the purpose of removing the contamination layer, wherein determination of the layer thickness takes place as described below.

According to a further aspect of the invention, the object is met by a method for determining the thickness of a contamination layer on the surface of an optical element that comprises a reflection-reducing or reflection-increasing layer system in the installed state in an optical system, comprising the steps of: (a) radiation of light with a plurality of wavelengths onto the optical element; (b) spectrally resolved detection of the light reflected by the surface for the purpose of determining the wavelength-dependent reflectivity of the optical element, and determining a first wavelength of minimum reflectivity when a contamination layer is present; (c) comparing the first wavelength with a second wavelength of minimal reflectivity that has been determined without a contamination layer; (d) determining the thickness of the contamination layer from the difference between the first and the second wavelengths, as well as from layer thicknesses and refractive indices of the individual layers of the layer system.

The wavelength-dependent reflectivity in the presence of a contamination layer differs significantly from the reflectivity without such a layer, namely in that the reflectivity in the first case is increased, as well as in that the wavelength of a minimum of the reflectivity is displaced. From the displacement of this wavelength, in the case of a known refractive index of the contamination layer (typically siloxane), as well as in the case of known refractive indices and layer thicknesses of the individual layers of the layer system, conclusions can be drawn in relation to the thickness of the contamination layer. In the case of more complicated layer systems, several minima of reflectivity can occur, wherein by balancing the shapes of the reflectivity graphs it can be ensured that only associated minima of reflectivity are compared with each other.

Further characteristics and advantages of the invention are provided in the following description of exemplary embodiments of the invention, in the figures of the drawing that show details which are significant in the context of the invention, and in the claims. Individual characteristics can be implemented individually per se, or they can be implemented to form several characteristics in any combinations in a variant of the invention.

BRIEF DESCRIPTION OF THE DRAWINGS

Exemplary embodiments are shown in the diagrammatic drawing and are explained in the description below, wherein in different figures the same reference characters are used for identical or similar elements. The following are shown.

DETAILED DESCRIPTION

Figure 1:
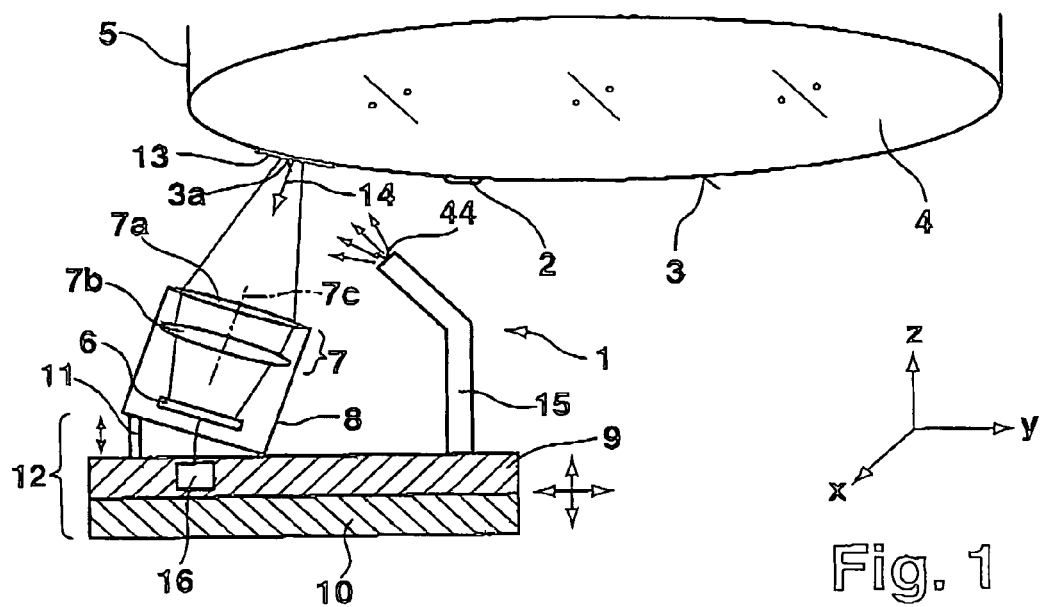
FIG. 1 a diagrammatic view of a lateral section of an embodiment of an examination system according to the invention for locating contamination on the surface of an optical element comprising magnifying imaging optics.

FIG. 1 diagrammatically shows an examination system 1 that is used for locating and, if applicable, for identifying contamination 2 on a surface 3 of an optical element 4. In this arrangement the optical element 4 is a lens that is transparent for radiation of a wavelength of 193 nm, with said optical element 4 being the closing element of a projection lens 5 for microlithography, which forms an essentially closed optical system of which only a section is shown in FIG. 1.

The examination system 1 comprises a CCD array as a spatially resolving detector 6 as well as imaging optics 7 that are formed by two lenses 7a, 7b that form a telescope arrangement for magnifying imaging of a surface sub-region 3a of the surface 3 on the detector 6 with an adjustable imaging scale. To this effect the first lens 7a can be moved relative to the second lens 7b in a direction along an optical axis 7c of the imaging optics by way of a suitable mechanism (not shown).

The imaging optics 7 together with the detector 6 are arranged in a common housing 8 and are affixed therein.

The housing 6 is arranged on a translational table 9 that is displaceably arranged by three linear motors (not shown) on a plate 10 along three axes (x, y, z) that are perpendicular in relation to each other. As an alternative to sliding the table 9 relative to the plate 10, the table can also be manually displaced along the three axes. On the table 9 a further linear motor is arranged, which drives a telescopic arm as a tilting mechanism 11 for tilting the housing 8 relative to the table 9 or to the plate 10 on an angle situated in the drawing plane. A further linear motor (not shown) with telescopic arm is used to tilt the housing 8 in a direction perpendicular in relation to the drawing plane.

The tilting mechanism 11, together with the table 9 and the plate 10, forms a movement mechanism 12 for unrestricted spatial orientation of the imaging optics 7 together with the detector 6. In this way a situation is achieved in which an object plane 13 of the examination system can always be positioned on the surface 3 of the optical element 4 such that a surface normal 14 of the curved surface 3 in the centre of the imaged surface sub-region is always arranged along the optical axis 7c of the imaging optics 7 so that the surface sub-region 3a that is viewed at the time can be imaged as a whole without any distortion. In order to illuminate the sub-region of the surface 3, which sub-region is viewed at a given time, a light source 15 is used, whose light emission area 44 is arranged between the optical element 4 and the imaging optics 7 and radiates light at an angle to the optical axis 7c of the imaging optics 7 laterally into the beam path. Furthermore, the examination system 1 comprises a data processing unit 16 for evaluating the measuring data of the detector 6. Possibly, the data processing unit 16 may not be able itself to evaluate the measuring data, but instead transmits this data, e.g. through an infrared interface, a cable or some other suitable device, to an external data processing device (PC etc.).

For the purpose of preparing a map of the entire surface 3 of the optical element 4 the housing 8 with the imaging optics 7 and the detector 6 carries out a scanning movement along the surface 3, wherein the surface normal 14 of the surface is always aligned so as to be perpendicular to the object plane 13 of the examination system 1. The travel path that is necessary for scanning the surface 3 can, for example, be stored in the data processing unit 16 for the respective type of optical element. Furthermore, if it is ensured that the examination system 1 is always installed in the same location in the optical system 5, in this way it is possible to do without the use of measuring devices for determining the distance between the examination system 1 and the surface 3. As an alternative, of course such measuring is also possible. The travel path along the optical element 4 is approximately 20 cm each in the x-direction and in the y-direction, as well as approximately 5 cm in the z-direction. The focal length, on the side of the object, of the imaging optics 7 is approximately 5 cm so that it can be ensured that the imaging optics 7 can be positioned at adequate spacing from the surface 3.

By means of scanning the surface 3 a two-dimensional image of the surface 3 can be produced. In particular when the surface roughness of the surface 3 exceeds the focal depth of the imaging optics 7, for each magnified sub-region of the surface 3 the housing 8 can be displaced perpendicularly in relation to the surface 3, as a result of which the position of the object plane 13 is varied perpendicularly to the surface 3 so that a three-dimensional map of the surface 3 can be produced, as will be described in more detail below in the context of FIG. 2 and FIG. 3.

Figure 2A:
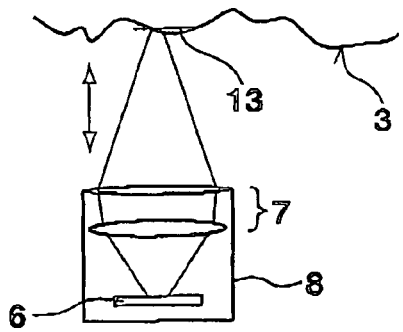
FIG. 2 a diagrammatic view of part of the examination system of FIG. 1 in a first distance from the surface (a) and a presentation of the magnified image, generated in this way, of a surface sub-region (b)
Figure 2B:
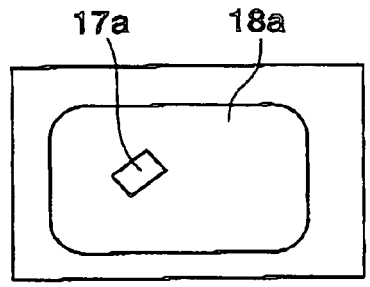
Figure 3A:
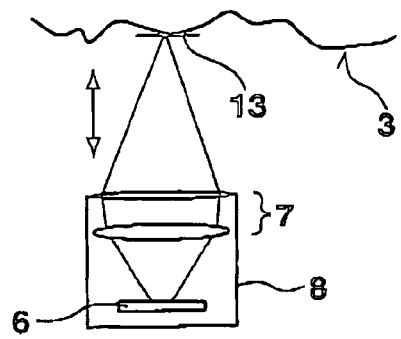
FIG. 3 a view analogous to that of FIG. 2 in a second distance from the surface.
Figure 3B:
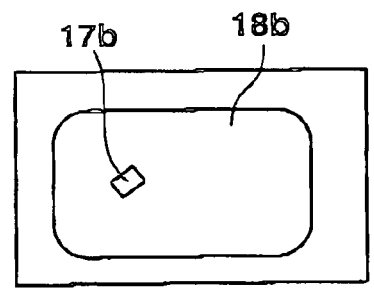

FIGS. 2a and 3a each show a section of FIG. 1 in which for the purpose of simplifying the view of the examination system 1 only the housing 8 with the detector 6 and the imaging optics 7 are shown, which imaging optics 7 image a section of the surface 3 on the detector 6 at an enlarged scale. The diagrams of FIGS. 2a and 2b differ by a different distance of the housing 8 perpendicularly from the surface 3, whose surface roughness is shown greatly magnified. By imaging the surface 3 with variable distance a three-dimensional profile of the surface 3 can be produced, as shown in FIGS. 2b and 3b.

FIG. 2b shows an enlarged surface sub-region 17a that was produced with the design shown in FIG. 2a. At this distance the object plane 13 of the imaging optics 7 intersects the surface 3 in a region that is larger than a surface sub-region 17b that was imaged at a greater distance. By scanning displacement of the housing 8 parallel to the surface 3, for each of the two distances a two-dimensional map 18a, 18b of the surface can be generated, which corresponds to a section of the surface at a certain height. From the two-dimensional maps, by superposition in the data processing unit 16 of FIG. 1 a three-dimensional height profile of the surface 3 can be produced.

Figure 4:
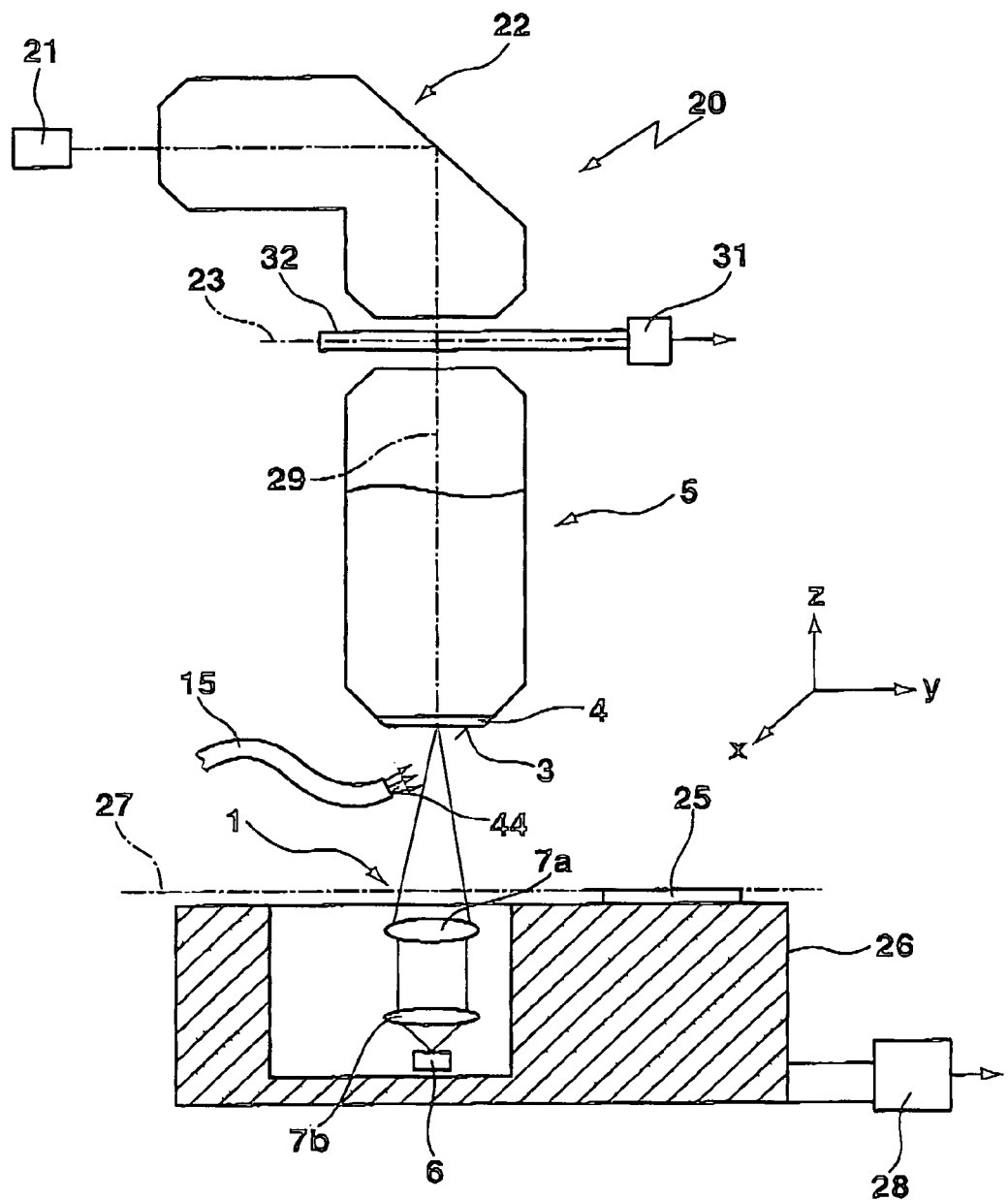
FIG. 4 an embodiment of projection illumination apparatus comprising an examination system with magnifying imaging optics, in a lateral section view.

The examination system 1 shown in FIG. 1 is mobile and is dimensioned such that it can, for example, be arranged in a substrate holder (wafer stage) or in a mask holder (reticle stage) of projection illumination apparatus; the maximum design height of said examination system is thus less than 50 cm. The examination system 1 can of course also be used for examining optical elements in other optical systems, e.g. in wafer inspection apparatus. Apart from the mobile design of the examination system 1, as shown in FIG. 1, the examination system 1 can also be installed permanently in projection illumination apparatus 20 for microlithography, as shown in FIG. 4 in the form of a wafer stepper for producing large-scale integrated semiconductor components.

The projection illumination apparatus 20 comprises an excimer laser 21 as a light source, with an operating wavelength of 193 nm, wherein other operating wavelengths, for example 248 nm, are also possible. An illumination system 22, arranged downstream, in its emission plane generates a large, sharply delimited, very homogeneously illuminated image field that matches the telecentric-lens requirements of a projection lens 5 that is arranged downstream.

Behind the illumination system 22 a device 31 for holding and manipulating a photomask 32 is arranged such that said photomask 32 is situated in an object plane 23 of the projection lens 5 and in this plane can be moved, for scanning operation, in a travel direction indicated by an arrow. Behind the plane 23, which is also known as the mask plane, the projection lens 5 follows, which projection lens 5 images an image of the photomask 3 at a reduced scale, for example at a scale of 4:1 or 5:1 or 10:1, onto a wafer 25 that comprises a photoresist layer. The wafer 25, which serves as a light-sensitive substrate, is arranged such that the plane substrate surface with the photoresist layer essentially coincides with an image plane 27 of the projection lens 5. The wafer is held by a device 26 that comprises a scanner drive 28 so as to move the wafer 25 synchronously with the photomask 23 parallel to said photomask 23. The device 26 also comprises manipulators in order to move the wafer both in z-direction parallel to an optical axis 29 of the projection lens, and in x- and y-directions perpendicular to this axis, wherein the travel path in z-direction is typically a few μm.

The projection lens 5 comprises a base plate as a closing element, which base plate is an optical element 4 adjacent to the image plane 27. The surface 3 of the optical element 4 is imaged onto a detector 6 by an examination system 1, wherein said examination system 1 essentially differs from the examination system 1 shown in FIG. 1 in that it is permanently integrated in the device 26 that serves as a movement mechanism for the examination system 1 so that the examination system 1 can be displaced along the axes x, y, z relative to the surface 3, wherein the drive 28 is modified when compared with conventional projection illumination apparatus such that movement by several centimeters in the z-direction is possible. In this case a tilting mechanism is not necessary because the surface of the optical element 4 is planar. A fibre-optical cable that is used as a light generating unit 15 is arranged such that a light emission area 44 is positioned laterally between the surface 3 of the optical element 4 and the device 26.

As an alternative to the design shown in FIG. 4 it is of course also possible to arrange the examination system 1 and the wafer 25 in separate units that are exchanged by a suitable controlling apparatus, depending on whether the projection illumination apparatus 20 is in illumination mode or in inspection mode. Instead of the design of the examination system as shown in FIG. 4, which examination system can travel using the drive 28, for the purpose of displacement the examination system 1 can also comprise a translational table of its own, as shown in FIG. 1, wherein the unit 26 is not displaced during measuring.

Of course, it is possible, in the unit 26 that carries the examination system 1, to also provide an additional unit (not shown) for cleaning the optical element 4, wherein possible embodiments for such cleaning units are for example shown in US 2004/0094115 A1. In this way, by means of the examination system 1 of FIG. 4, first by magnified imaging of the surface 3, precise location of the contamination located on said surface 3 can be carried out, which contamination can subsequently be removed in a targeted manner by the unit for cleaning the surface 3.

In particular, by magnifying imaging, the microstructure of the contamination can be clarified, so that such contamination is identified for example as salts, polymers etc., and can be removed with a suitable cleaning process. Furthermore, it is also possible to detect any defects (e.g. scratches) on the surface 3, which are difficult or impossible to remove by normal cleaning methods. In this case, instead of cleaning, for example replacing the optical element 4 may be necessary.

Figure 5:
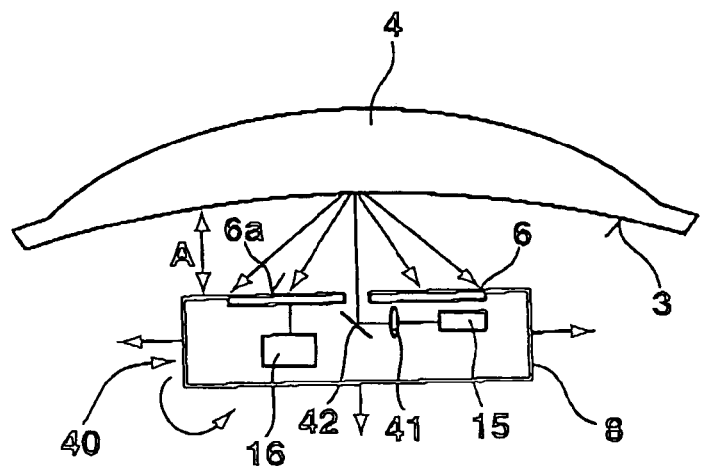
FIG. 5 an embodiment of an examination device according to the invention for radiating examination light onto the surface of an optical element, and for detection, on a spatially resolving detector, of the light scattered by the surface.
Figure 6:
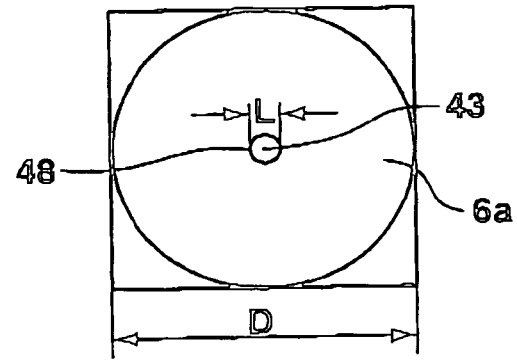
FIG. 6 a view of the surface of the detector of FIG. 5.

Apart from examining optical surfaces by means of microscopy, as described above, measuring the spatially resolved reflection, i.e. of the scattered light reflected by a surface, may also provide information about the arrangement and nature of contamination. An examination device 40 suitable for this purpose is shown in FIG. 5. By means of a suitable movement mechanism (not shown), the examination device 40 is displaceable along three axes and is rotatable on two further axes, as indicated by arrows, with said examination device 40 being spaced apart from the surface 3 by the distance A. The examination device comprises an IR laser as a light generating unit 15, which generates a laser beam that by means of beam guidance and focussing optics, which are shown in a simplified manner by a lens 41 and a mirror 42, is directed, in a direction perpendicular in relation to the surface 3, onto the optical element 4 where it is focused. The light scattered by the surface 3 impinges upon a spatially resolving detector 6 (CCD array) with a circular detector area 6a (not shown in FIG. 6) of a diameter D. The detector area 6a comprises a central recess 48 with a diameter L, through which central recess 48 the primary beam that is directed onto the surface can pass, thus serving as a light emission area 43. The recess 48 is used at the same time to accommodate the beam that is directly reflected by the surface, which beam does not impinge upon the detector surface 6a and thus prevents any saturation of the detector 6. In order to make possible such return of the non-scattered beam the primary beam has to impinge upon the optical element 4 essentially perpendicularly in relation to the surface 3, to which effect the examination system 40 is suitably positioned by means of the movement mechanism. Furthermore, the distance A from the surface 3 should be selected such that as far as possible the entire reflected light beam enters the recess 43 and does not impinge upon the detector area 6a.

The distance A from the surface 3 is selected such that an interesting angular range of the scattered light impinges upon the detector area 6a. This angular range is limited towards the top by a maximum detectable angle $\alpha_{max}$, which is calculated from the equation $\tan(\alpha_{max})=D/(2A)$. Correspondingly, for the minimum angle $\alpha_{min}$ at which scattered-light measuring can take place $\tan(\alpha_{min})=L/(2A)$ applies, so that by a suitable selection of the distance A the angular range for scattered-light measuring can be set between these two values: $\alpha_{min}<\alpha<\alpha_{max}$. The scattered light registered by the detector 6 in this angular range is evaluated by a data processing unit 16 that is connected to the detector 6 for locating contamination on the surface 3. By displacing the examination device 40 parallel in relation to the surface 3, the point at which the primary beam impinges upon the surface can be displaced, and in this way a two-dimensional scattered-light map can be produced.

Figure 7:
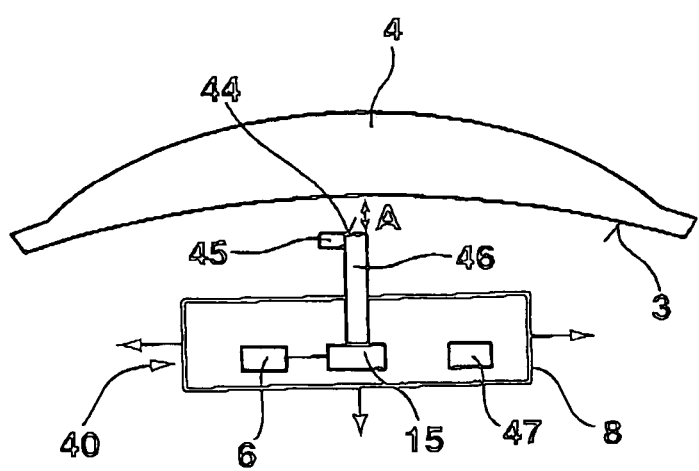
FIG. 7 an embodiment of an examination device according to the invention with a fibre-optical light guide for radiating examination light onto the surface of an optical element, and for returning the light reflected by the surface.

As an alternative or in addition to spatially resolving measuring of the scattered light, measuring of the spectral characteristics of the light reflected by the surface 4 can also be carried out, e.g. by means of a design of an examination device 40 shown in FIG. 7, which examination device 40 differs from the examination device 40 shown in FIG. 5 in that the feeding of light from the light generating unit 15 to the surface 3 does not take place by means of beam guidance optics 41, 42 but instead by a fibre-optical light guide 46 (optical fibre cable). In this arrangement the surface 3 of the optical element 4 comprises a multicoated anti-reflex system. Apart from feeding light to the surface 3, the fibre-optical light guide 44 is also used to return the light reflected by the surface 3, which light is decoupled from the light generating unit 15 and is fed to a detector 6. A light emission area 44 of the fibre-optical light guide 46 is located in the near field, i.e. at a distance A of less than 1 mm from the surface 3. In order to keep this distance A as constant as possible during scanning of the surface 3, a distance measuring device 45 for measuring the optical distance in the examination device 40 is provided, which distance measuring device 45 is coupled to a control device 47 for setting the distance. In this case the light generating unit 15 and the detector 6 are designed to generate or detect light at several wavelengths, as a result of which spectrally resolved measuring of the reflectivity of the surface 3 can be carried out. This makes it possible, in particular, to draw conclusions relating to the nature of thin contamination layers (films) that are located on the surface 3. The material from which such layers are made is usually known (e.g siloxane); e.g. in the case of a closing element of the projection lens of projection illumination apparatus said material depends on the substances that are used as a photoresist. If the type of contamination is known, the refractive index of the contaminating substance can be determined. If said refractive index and the wavelength-dependent reflection are known, conclusions relating to the thickness of the contamination layer can be drawn.

Figure 14:
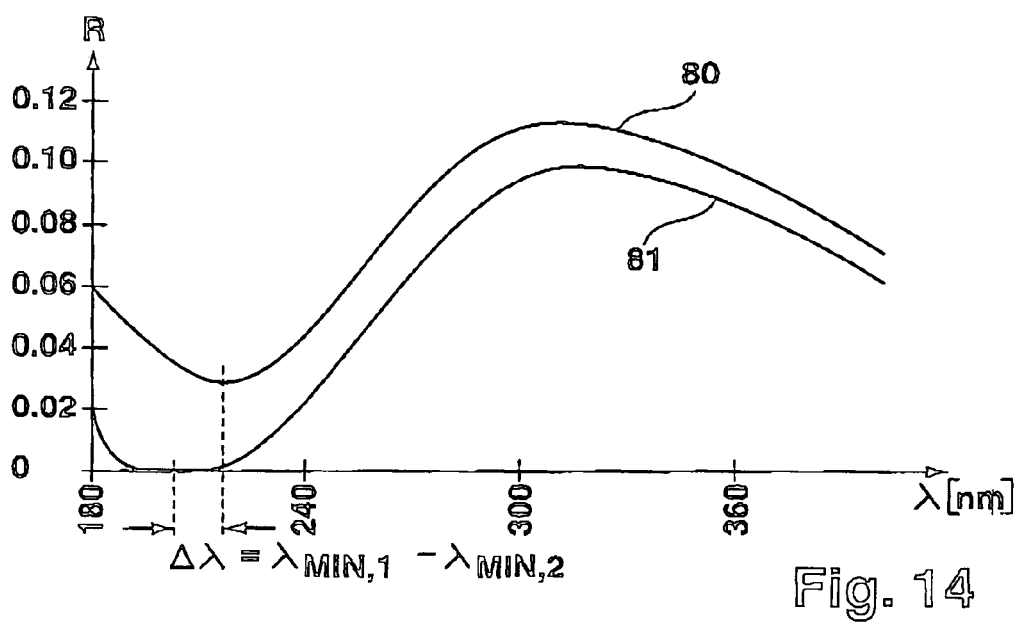
FIG. 14 a view of the wavelength-dependent reflectivity of an optical element with and without the presence of a contamination layer.

FIG. 14 shows the wavelength-dependent reflectivity R, depending on the wavelength λ (in nm), for the optical element 4 shown in FIG. 7 without such a contamination layer (first, lower graph 81) and with such a layer (second, upper graph 80). The thickness of the contamination layer can be calculated from the difference $\Delta\lambda$ of the wavelengths $\lambda_{min, 1}$ and $\lambda_{min, 2}$, of the minima of these two graphs 80, 81. To this effect the refractive index of the contamination layer has to be known, as do the characteristics of the multilayer system, i.e. the refractive indices and thicknesses of the individual layers of the system. If all these values are known, in a suitable way the thickness of the contamination layer can be calculated or determined by means of simulation. If the refractive index of the contamination layer is not known, it can be estimated. In this way the thickness of the contamination layer can be determined to within a few nm.

The examination devices 40 shown in FIG. 5 and FIG. 7 can either be mobile in design or can be permanently installed as has been described in more detail in connection with the examination system 1 in the context of FIGS. 1 and 4.

Apart from optical examination of surfaces of optical elements for contamination, it is also possible to obtain information about the nature of contamination of optical elements arranged in projection illumination apparatus by taking samples. This is explained in more detail below with reference to FIG. 8 to FIG. 12, wherein in FIG. 8 and FIG. 9 in each instance an optical closing element 4 of a projection lens 5 of projection illumination apparatus is examined for contamination 2, while in FIG. 10 to FIG. 12 the inspection of a closing element of an illumination system 22 is carried out.

To this effect a sample is taken, by means of a manipulator 50, from the surface 3 of the element 4, and is placed in a sample container 53. The sample taken can then, either manually or in an automated manner, be removed from the sample container and conveyed to a chemical analysis device. As an alternative, such a device can be integrated in the manipulator 50 itself. In this arrangement the manipulator is held on a table 9 which together with a plate (not shown) constitutes a movement mechanism as explained in more detail in the context of FIG. 1.

Figure 8:
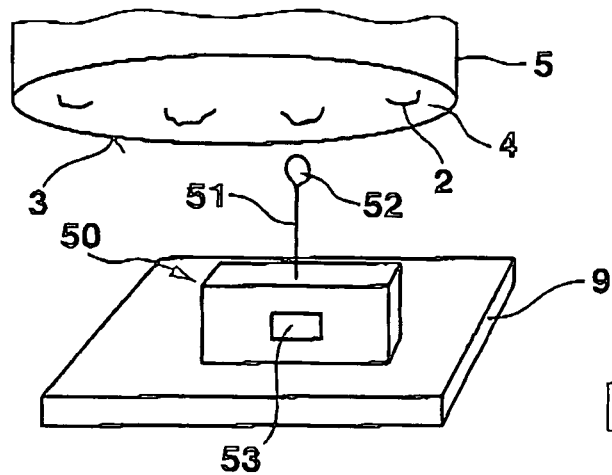
FIG. 8. a section of projection illumination apparatus according to the invention with a manipulator with a wire loop for taking a sample of contamination on a surface.

In the design of the manipulator 50, as shown in FIG. 8, said manipulator 50 comprises a detachment unit 51 for taking a sample from the surface 3 by mechanical contact by means of a wire loop 52, with the diameter of said loop 52 being variable so that by tightening the wire loop 52 a sample can be taken. An arm of the detachment unit 51, to which arm the wire loop 51 is affixed, can be shortened so that the sample can be placed in the sample container 53.

Figure 9:
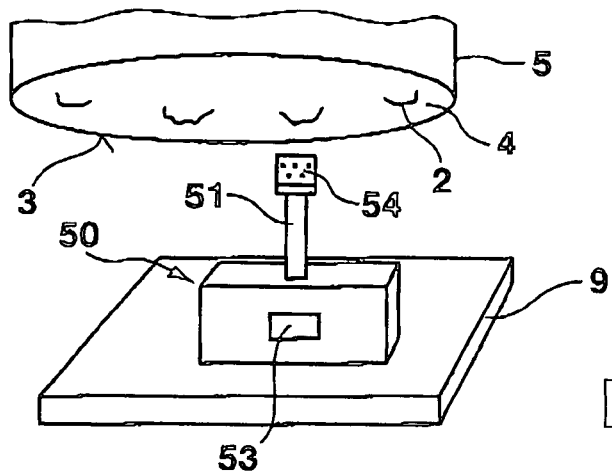
FIG. 9 a view analogous to that of FIG. 8 with a manipulator with a woven fabric for taking the sample.

In the design of the manipulator 50, as shown in FIG. 9, the wire loop 52 is formed by a woven fabric 54 that has been impregnated with solvent, which woven fabric 54, by shortening of the arm of the sampling unit 51, is placed in the sample container 53 for further examination. In this arrangement, preferably water is used as a solvent.

Figure 10:
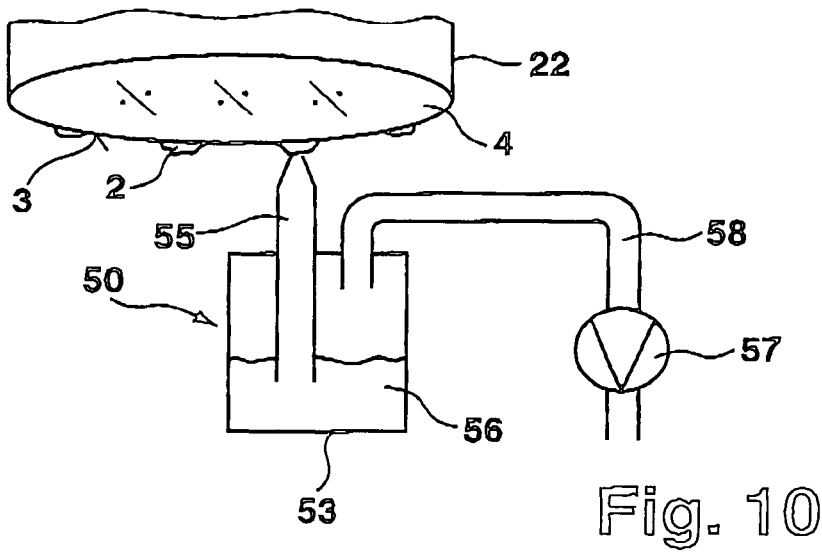
FIG. 10 a lateral section view analogous to those of FIGS. 8 and 9 with a manipulator with a capillary for sucking a sample from the surface.

In a further design of the manipulator 50, shown in FIG. 10, said manipulator 50 comprises a capillary 55 that communicates with the sample container 53. A tip of the capillary 55 is placed underneath the contamination and said contamination is sucked into the sample container 53 in that by means of a vacuum pump 57, which is arranged in a suction pipe 58 that also communicates with the sample container 53, negative pressure is generated. The sample is dissolved in a solvent 56 that is arranged in the sample container 53 and from there can be removed by way of an outlet (not shown). Before further samples are taken, the solvent can of course be completely replaced. As an alternative it is of course also possible not to provide any solvent in the sample container 53 so that the sample can be removed as a solid material from said sample container 53.

Figure 11:
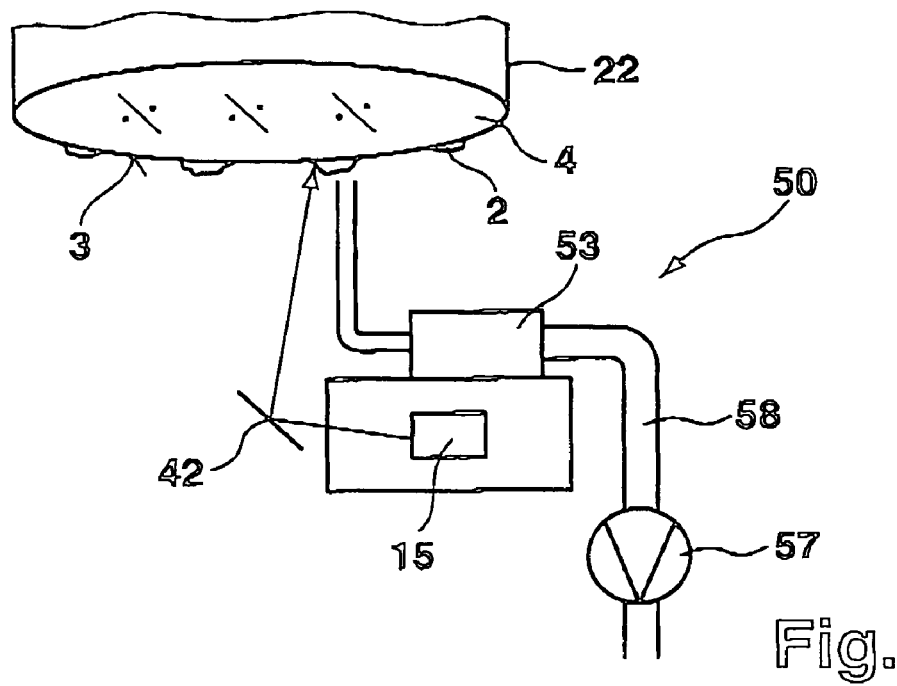
FIG. 11 a lateral section view analogous to those of FIGS. 8 to 10 with a manipulator with an IR laser for evaporating part of the contamination.

In an alternative design of the manipulator 50, shown in FIG. 11, an IR laser as a radiation source 15 is used as a detachment unit for removing the sample from the surface. By way of a mirror 42, light is radiated onto a contaminated location on the surface 3. As a result of the light impingement, part of the contamination is evaporated and by way of a suction pipe 58 that communicates with a vacuum pump 57 is placed into an absorber tube that serves as a sample container 53.

Figure 12:
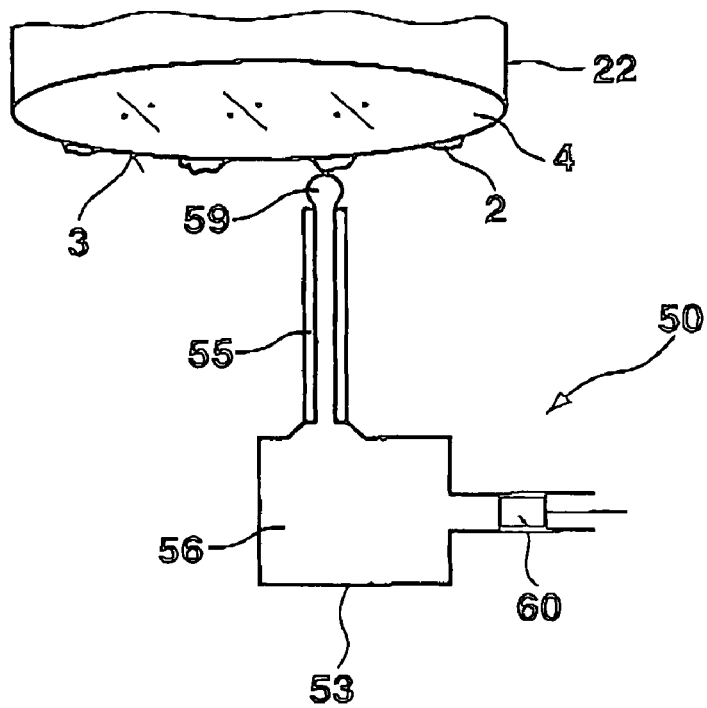
FIG. 12 a lateral section view analogous to those of FIGS. 8 to 11 with a manipulator with a capillary for applying a solvent.

In a further design of the manipulator 50, shown in FIG. 12, the piston of a pump 60 is displaced so as to let a solvent droplet 59 issue from a capillary 55, which solvent droplet 59 moistens the contamination. By moistening the contaminating substances with the solvent droplet 59, some of these substances are dissolved and, by sliding the piston back into the capillary 55, can be sucked in and placed in the sample container that contains solvent 56.

The designs of the manipulator 50, which designs have been described in the context of FIGS. 8 to 12, provide an advantage in that a sample of the contamination 2 can be taken without damaging the surface of the optical element 4. Preferably, the manipulator 50 is used together with the examination system 1 or the examination device 40 so that the location of sampling can be determined in a targeted manner. To this effect the examination system 1, the examination device 40 and the manipulator 50 are preferably arranged on a shared movement mechanism (not shown).

Figure 13:
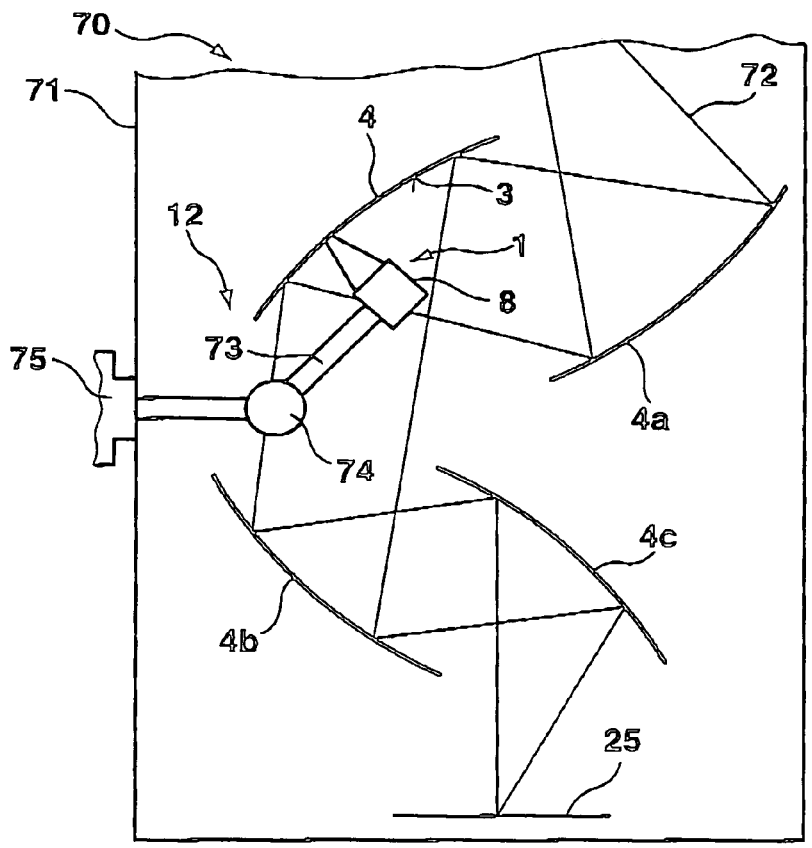
FIG. 13 a view of a vacuum chamber of an embodiment of EUV projection illumination apparatus according to the invention with an examination system in the interior of the chamber.

Although the above description deals with the inspection of transparent optical elements, it is understood that the inspection options as described above can also be applied in the case of reflective optical elements as used, for example, in projection illumination apparatus for the EUV (extreme ultraviolet) range, in particular at wavelengths of approximately 13.5 nm, in which projection illumination apparatus there is no material available that provides adequate optical transmission. A detail of such EUV projection illumination apparatus 70 is shown in FIG. 13, with the components of such EUV projection illumination apparatus being arranged in a vacuum chamber 71. The vacuum chamber 71 comprises four mirrors 4, 4a-c, which in illumination mode are used to deviate a light ray 72 from a mask (not shown) onto a substrate 25, wherein said mirrors 4, 4a-c at the same time cause size-reducing imaging of a structure, which is located on the mask, onto the substrate 25.

It is advantageous if for the purpose of inspecting the mirrors 4, 4a-c there is no need to release the vacuum in the vacuum chamber 71. In order to avoid this, an examination system 1 attached to a port 75 is fully integrated in the vacuum chamber 71. The port 75 is connected to a joint 74 by way of a telescopic arm, which joint 74 is connected to a further telescopic arm 73, which is swivellable, on which a housing 8 with the components of the examination system 1, which components are shown in FIG. 1, is arranged, wherein the bearing arrangement of the housing with the swivellable arm 73 serves as a movement mechanism 12. By way of the joint 74 and the swivellable telescopic arm 73, all four mirrors 4, 4a-c in the vacuum chamber 71 can be positioned for inspection. In illumination mode the swivellable telescopic arm 73 can be led out of the beam path so that illumination of the substrate 25 can be carried out. In addition, or as an alternative, it is of course possible for the examination device 40 or some suitable unit for removing contamination to be attached to the telescopic arm.

Figure 15:
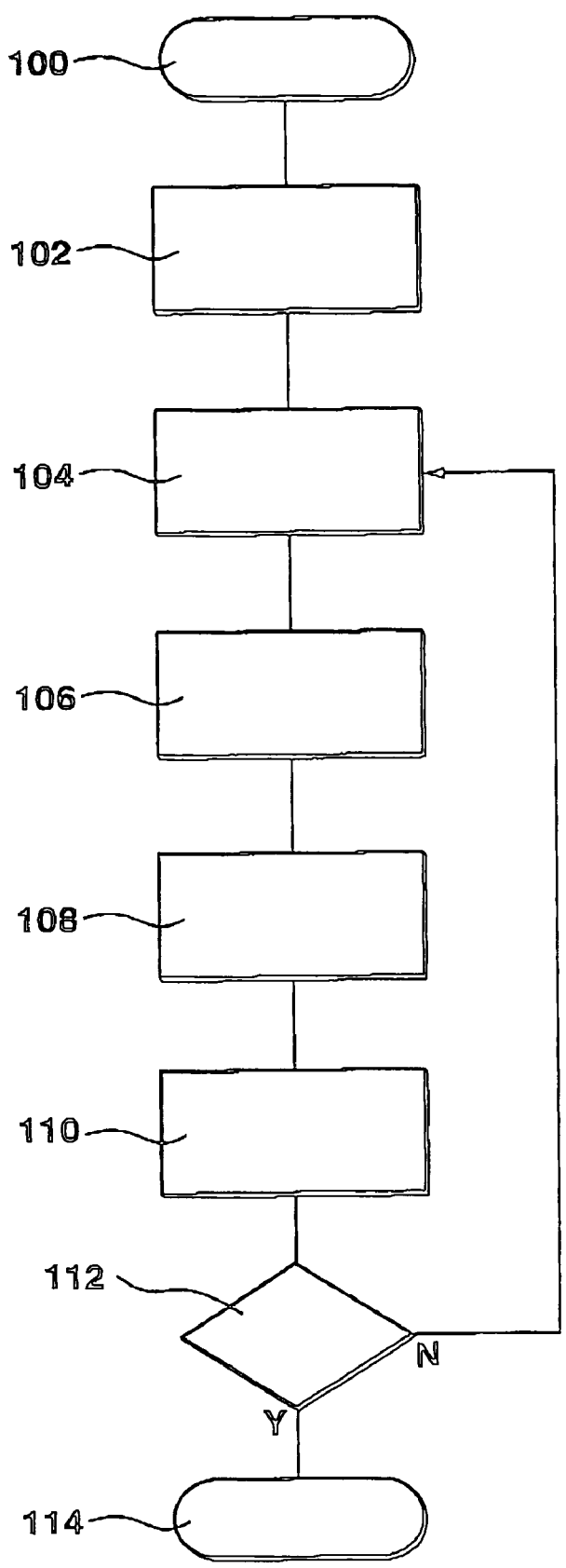
FIG. 15 a view of a variant of a method according to the invention for removing contamination from the surface of an optical element.

With a combination of an examination system, an examination device or a manipulator with a unit for removing contamination, advantageously a method for removing contamination from the surface of an optical element installed in an optical system can be carried out, with the sequence of said method being explained in more detail below with reference to a flow chart shown in FIG. 15.

The method starts with a step 100. In a subsequent step 102 measuring data is acquired, which data is significant in relation to the nature of contamination on the surface of the optical element. The measuring data can preferably be acquired by means of one of the inspection methods presented above, i.e. by microscopy, spectrally or spatially resolved measuring of radiation reflected by the optical element, or by taking samples from the surface.

In a subsequent step 104 the measuring data is evaluated and compared with known data that is significant in relation to the nature of contamination. This takes advantage of the fact that certain types of contamination have characteristic microscopic structures so that by comparison with known data it becomes possible to determine the type of contamination. A table with the types of contamination and the data that is characteristic for these types can be produced in a method-related step that precedes step 102.

Depending on the result of the comparison in step 104, in a subsequent step 106 a cleaning method for removing the contamination is then selected from a group of cleaning methods. The cleaning methods used in this procedure can preferably include ultrasonic cleaning, contact cleaning, applying a cleaning solution, exposure to radiation, application of a cleaning gas, and plasma cleaning. In a further step 108 the contamination is removed by applying the selected cleaning method. In a further method-related step 110, which step corresponds to step 102, measuring data is acquired again, which data is significant in relation to the nature of contamination on the surface of the optical element. In this way the success of the selected cleaning method can be monitored. In a subsequent step 112, depending on the success of cleaning, either the method is terminated in a step 114, or step 104 is repeated, in which a comparison of the determined data with known data takes place. In this step, if applicable, it can be taken into account that the selected cleaning method was only partly able to dissolve the contamination, and, if applicable, based on this recognition some other cleaning method can be selected. However, it is also possible for the same cleaning method to be carried out again, for example if it is found that the duration of the period of time required during the first cleaning process was insufficient.

In summary, the present invention makes it possible to determine the nature of contamination on optical elements in the installed state in optical systems, in particular in relation to its topography and composition, wherein information obtained in this manner can be taken into account e.g. during cleaning of the optical elements.

What is claimed is:

1. An examination system for locating contamination on an optical element installed in an optical system, which examination system comprises:
    a spatially resolving detector,
    magnifying imaging optics for magnified imaging of a surface sub-region of the optical element on the spatially resolving detector, as well as
    a movement mechanism for displacing the imaging optics of the examination system together with the detector of the examination system relative to the optical system in which the optical element is installed, such that any desired surface sub-region of the surface can be imaged at magnifications,
    in which examination system the movement mechanism comprises a tilting mechanism for tilting the imaging optics together with the detector relative to the surface of the optical element, such that the normal vector of the sub-region of the surface which is imaged at magnification is perpendicular to an object plane of the imaging optics.

2. The examination system according to claim 1, in which examination system the movement mechanism is a motorized movement mechanism.

3. The examination system according to claim 1, in which examination system the movement mechanism comprises two translatory drives for displacing the imaging optics together with the detector along two axes situated in a shared plane.

4. The examination system according to claim 3, in which examination system the movement mechanism comprises a third translatory drive for displacing the imaging optics together with the detector along a third axis, which is not situated in the shared plane.

5. The examination system according to claim 1, which examination system further comprises: a light generating unit with a light emission area for radiation of illumination light onto the optical element.

6. The examination system according to claim 1, in which examination system the focal length of the imaging optics, which focal length is on the side of the object, measures more than 3 cm.

7. The examination system according to claim 1, in which examination system the imaging optics comprise zoom optics for variable setting of the magnification.

8. The examination system according to claim 1, in which examination system the detector is a CCD array.

9. The examination system according to claim 1, which examination system further comprises a data processing unit that is connected to the detector, for evaluating measuring data of the detector.

10. The examination system according to claim 1, further comprising a unit for removing contamination.

11. The examination system according to claim 1, which examination system is dimensioned such that it can be accommodated in a holder of an optical device.

12. A method for locating contamination on the surface of an optical element using an examination system according to claim 1, the method comprising the steps of:
    (a) magnifying imaging of the entire surface of the optical element or of a surface sub-region of the optical element, and
    (b) detecting the magnified image of the entire surface or of the surface sub-region.

13. The method according to claim 12, in which method steps (a) and (b) are carried out in relation to a plurality of surface sub-regions, the method further comprising the step of:
    (c) producing a map of the surface from the plurality of magnified images.

14. The method according to claim 13, in which method for each surface sub-region the distance between the object plane of the magnifying imaging optics and the surface is varied in a direction perpendicular to the surface, and in step (c) a three-dimensional map of the surface is produced from the plurality of magnified images.

15. The method according to claim 13, in which method the enlarged image detected in step (b), or the map produced in step (c), is evaluated to locate the contamination.

16. An optical device comprising:
    an optical system,
    at least one optical element installed in the optical system, and an examination system for locating contamination on the optical element, wherein the examination system comprises:

a spatially resolving detector, and magnifying imaging optics for magnified imaging of the entire surface of the optical element or of a surface sub-region of the optical element on the spatially resolving detector, and a movement mechanism for displacing the imaging optics together with the detector relative to the optical system in which the optical element is installed, such that any desired surface sub-region can be imaged at magnification, in which optical device the movement mechanism comprises a tilting mechanism for tilting the imaging optics together with the detector relative to the surface such that a normal vector of the sub-region of the surface which is imaged at magnification is perpendicular to an object plane of the imaging optics.

17. The optical device according to claim 16, in which optical device the movement mechanism is a motorized movement mechanism.

18. The optical device according to claim 16, in which optical device the movement mechanism comprises two translatory drives for displacing the imaging optics together with the detector along two axes situated in a shared plane, relative to the optical element.

19. The optical device according to claim 18, in which optical device the movement mechanism comprises a third translatory drive for displacing the imaging optics together with the detector along a third axis, which is not situated in the shared plane.

20. The optical device according to claim 16, in which optical device the examination system comprises a light generating unit with a light emission area for radiation of illumination light onto the optical element.

21. The optical device according to claim 16, in which optical device the focal length of the imaging optics, which focal length is on the side of the object, measures more than 3 cm.

22. The optical device according to claim 16, in which optical device the imaging optics comprise zoom optics for variable setting of the magnification.

23. The optical device according to claim 16, in which optical device the detector is a CCD array.

24. The optical device according to claim 16, in which optical device the examination system comprises a data processing unit that is connected to the detector for evaluating the measuring data of the detector.

25. The optical device according to claim 16, which optical device comprises a unit for removing contamination.

26. The optical device according to claim 16, in which the optical element to be examined is a closing element of a closed optical system in which the optical element is installed.

27. The optical device according to claim 26, in which optical device the optical element to be examined is a closing element of a projection lens which is arranged so as to face the light-sensitive substrate of the projection lens.

28. The optical device according to claim 16, in which optical device the optical element is arranged in the interior of a vacuum chamber, and the examination system is arranged outside the vacuum chamber.

29. The optical device according to claim 16, in which optical device the examination system and the optical element are arranged in the interior of a vacuum chamber.

* * * * *